United States Patent [19]

Wagner et al.

[11] Patent Number: 5,403,957
[45] Date of Patent: Apr. 4, 1995

[54] METHOD FOR PREPARING N-FLUOROSULFONIMIDES

[76] Inventors: William J. Wagner, S-5419 Roberts Rd., Hamburg, N.Y. 14075; George A. Shia, 71 October La.; Andrew J. Poss, 145 Charter Oaks #2, both of Amherst, N.Y. 14228

[21] Appl. No.: 963,870

[22] Filed: Oct. 20, 1992

[51] Int. Cl.$^6$ .................. C07C 311/15; C07C 311/21; C07C 311/00; C07D 285/01; C07D 291/04
[52] U.S. Cl. ........................................ 564/82; 548/123
[58] Field of Search ........................... 564/82; 548/123

[56] References Cited

U.S. PATENT DOCUMENTS

| | | | |
|---|---|---|---|
| 2,341,614 | 2/1944 | Hentrich et al. | 564/82 |
| 4,387,222 | 6/1983 | Koshar | 548/123 X |
| 4,479,901 | 10/1984 | Barnette, I | 564/82 |
| 4,510,324 | 4/1985 | Rossi et al. | 564/82 |
| 4,697,011 | 9/1987 | DesMartelli, I | 548/123 X |
| 4,828,764 | 5/1989 | DesMarteau, II | 560/80 |
| 4,900,867 | 2/1990 | Wikes et al. | 564/91 |
| 4,973,697 | 11/1990 | Umemoto et al. | 546/295 |
| 5,003,074 | 3/1991 | Allmendinger et al. | 548/206 |
| 5,072,040 | 12/1991 | Armand, I | 564/82 |
| 5,081,249 | 1/1992 | Umemoto | 546/294 |

FOREIGN PATENT DOCUMENTS

| | | | |
|---|---|---|---|
| 0211578 | 2/1987 | European Pat. Off. | 564/82 |
| 0364340 | 4/1990 | European Pat. Off. | 564/82 |
| 0765524 | 9/1952 | Germany | 564/82 |
| 0865446 | 2/1953 | Germany | 564/82 |
| 0874446 | 4/1953 | Germany | 564/82 |
| 0054490 | 1/1968 | Poland | 564/82 |

OTHER PUBLICATIONS

Synlett, No. 3, Mar. 1991 Stuttgart, DE, pp. 187–189, E. Differding et al., "N-Fluorobenzenesulfonomides: A Practical Reagent for Electrophilic Fluorinations".
D. Barton et al., J. Chem Soc. Perkin 1, 732–738 (1974).
M. Seguin et al., J. of Fluorine Chem. 15 201–211 (1980).
C. Schack et al., J. of Fluorine Chem. 18, 363–373 (1981).
W. Barnette, II J. Am. Chem. Soc. 106, 452–454 (1984).
J. Foropoulous, Jr. et al., Inorg. Chem. 23, 3720–3723 (1984).
S. Lee et al., J. Am. Chem. Soc. 108, 2445–2447 (1986).
T. Umemoto et al., Tetrahedron Letters 27(28), 3271–3274 (1986).
S. Singh et al., J. Am. Chem. Soc. 109, 7194–7196 (1987).
D. Differding et al., Tetrahedron Letters 29(47), 6087–6090 (1988).
R. Banks et al., I J. of Fluorine Chem. 46, 297–305 (1990).
Synthesis and characterization of N-fluoroalkylsulfonamides: by Aleinikov, A. A. et al. which appeared in J. Fluorine Chemistry, vol. 58 Aug.–Sep./1992 p. 141.
Chemistry Department, University of Manchester Institute of Science and Technology, R. E. Banks, A. Khazaei, 1990, N-Halogeno Compounds, Part II etc.
Tetrahedron Letters, vol. 32, No. 13, pp. 1631–1634, 1991, F. A. Davis, W. Han, N-Fluoro-O-Benzenedisulfonimide: A Useful New Fluorinating Reagent.

Primary Examiner—Floyd D. Higel

[57] ABSTRACT

The present invention relates to a process of preparing N-benzenesulfonimides comprising reacting an alkali metal salt of a sulfonimide with fluorine in the presence of water or water/organic solvent mixtures. N-fluorosulfonimides are useful as fluorinating agents. The N-fluorosulfonimides allow the introduction of fluorine into organic compounds under mild conditions.

23 Claims, No Drawings

METHOD FOR PREPARING N-FLUOROSULFONIMIDES

BACKGROUND OF INVENTION

The present invention relates to an improved method for preparing N-fluorosulfonimides. N-fluorosulfonimides and related compounds can be used in the fluorination of nucleophilic organic compounds such as enolethers, aromatics, and organometallic species.

Fluorine substituents are playing an increasingly important role in the search for new pharmaceutical and agrochemical agents because they modify physicochemical properties and the biological activity of target molecules. See for example BIOMEDICINAL ASPECTS OF FLUORINE CHEMISTRY, Elsevier Biomedical Press, 1982.

Electrophilic fluorination agents allow the introduction of fluorine into target molecules under mild conditions. Fluorination agents containing a nitrogen-fluorine bond are known. U.S. Pat. No. 5,003,074 and E. Differding et al., "New Fluorinating Reagents—The First Enantioselective Fluorination Reaction", *Tetrahedron Letters* 29(47), 6087 (1988) teach the use of N-fluorosultams in the selective fluorination of carbanions. N-Fluorosultams are disadvantageous because they are insufficiently reactive to fluorinate less reactive nucleophiles such as enol ethers and aromatics.

More reactive N-F reagents are known to react with such nucleophiles, but they suffer from other deficiencies. C. Schack et al., "Substitution and Addition Reactions of $NF_4BF_4$ with Aromatic Compounds", *J. Fluorine Chem.* 18, 363 (1981) teach that $NF_4BF_4$ is a useful fluorination agent but access to the $NF_4BF_4$ is difficult.

T. Umemoto et al., "N-Fluoropyridinium Triflate and its Analogs, The First Stable 1:1 Salts of Pyridine Nucleus and Halogen Atom", *Tetrahedron Letters* 27(28), 3271 (1986) and T. Umemoto et al., "Power and Structure-Variable Fluorinating Agents—The N-Fluoropyridinium Salt System", *J. Am. Chem. Soc.* 112, 8563 (1990) teach that N-fluoropyridinium salts are useful fluorinating agents but unfortunately they undergo side-reactions with carbanionic nucleophiles.

R. Banks et al., "N-Halogeno Compounds—Part II—Perfluoro-[N-fluoro-N-(4-pyridyl)-methanesulphonamide]—A Powerful New Electrophilic Fluorinating Agent", *J. Fluorine Chem.* 46, 297 (1990) teaches that perfluoro-[N-fluoro-N-(4-pyridyl)methanesulphonamide] is a useful fluorinating agent. Unfortunately, the preparation of perfluoro-[N-fluoro-N-(4-pyridyl)methanesulphonamide] involves at least six steps and perfluoro-[N-(4-pyridyl)methanesulphonamide] cannot be used with aromatic solvents such as benzene or toluene because it reacts with these solvents.

N-Fluorosulfonamides are known to be useful as fluorinating agents. For example, U.S. Pat. No. 4,479,901; M. Sequin et al., "Action de $CF_3$ of Sur Des Aziridines N-Substituees", *J. Fluorine Chem.* 15, 201 (1980); W. Barnette, "N-Fluoro-N-alkylsulfonamides: Useful Reagents for the Fluorination of Carbanions", *J. Am. Chem. Soc.* 106, 452 (1984); and U.S. Pat. No. 4,900,867 teach that N-fluoro-N-alkylsulfonamides such as N-fluoro-N-neopentyl-p-toluenesulfonamide are useful in the fluorination at a carbon atom of a carbanion. S. Lee et al., "Stereospecific Synthesis of Alkenyl Fluorides (with Retention) via Organometallic Intermediates", *J. Am. Chem. Soc.* 108, 2445 (1986) teach that N-fluoro-N-alkylsulfonamides such as N-tert-butyl-N-fluorobenzenesulfonamide are useful in the fluorination of alkenyl iodides. N-Fluoro-N-alkylsulfonamides are disadvantageous to use because in preparation, N-fluoro-N-alkylsulfonamides are difficult to isolate and thus, require either column chromatography or low pressure distillation and organometallics or strongly basic anions cause β-elimination of HF from the reagent.

U.S. Pat. No. 4,828,764; J. Foropoulos, Jr. et al., "Synthesis, Properties, and Reactions of Bis((trifluoromethyl)sulfonyl)imide, $(CF_3SO_2)_2NH$", *Inorg. Chem,* 23, 3720 (1984).; S. Singh et al., "N-Fluoroperfluoroalkylsulfonimides: Remarkable New Fluorination Reagents", *J. Am. Chem. Soc.* 109, 7194 (1987); G. Resnati et al., "N-Fluorobis[(trifluoromethyl)sulfonyl]imide: An Efficient Reagent for the α-Fluorination of Functionalized Carbonyl Compounds", *J. Org. Chem.* 56, 4925 (1991); and D. Desmarteau et al., "N-Fluoro-N-Bis(trifluoromethanesulfonyl)imide—An Improved Synthesis", *J. Fluorine Chem.* 52, 7 (1991) teach that N-fluoroperfluoroalkylsulfonimides such as N-fluorobis(trifluoromethanesulfonyl)imide are useful in the fluorination of organic compounds. Unfortunately, N-fluoroperfluoroalkylsulfonimides are disadvantageous to use because a five step synthesis for their preparation is required, they are very hydroscopic, they cannot be used with aromatic solvents such as benzene or toluene because they react with these solvents, and they require special handling because they react with glass.

F. Davis et al., "N-Fluoro-o-benzenedisulfonimide: A Useful New Fluorinating Reagent", *Tetrahedron Letters* 32(13), 1631 (1991) teach that N-fluoro-o-benzenesulfonimide is useful in the fluorination of enolates and carbanions.

N-Fluoro-p-fluoro-benzenesulfonimide is known from D. Barton et al., *J. Chem. Soc. Perkin Trans.* 1, 732 (1974) but the reference does not teach any use for N-fluoro-p-fluoro-benzenesulfonimide.

Thus, there was a need in the art for a new electrophilic fluorinating agent which is easy to make and fluorinates less reactive nucleophiles. To a great extent such need was met by the novel fluorinating agents disclosed in the commonly assigned U.S. application Ser. No. 843,692 filed Feb. 28, 1992. Surprisingly, it was found that these N-fluorosulfonimides (See Formula I infra) behave as electrophilic fluorinating agents which combine safe handling and easy access with the capacity to fluorinate nucleophiles ranging from aromatics to carbanions.

The previous art prepared N-fluorosulfonimides by basically two methods. One method involved the preparation of N-fluorosulfonimides by direct fluorination of the imide. The direct fluorination is depicted by the following equation.

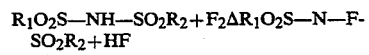

As can be seen, the fluorine replaces the imido hydrogen yielding the N-fluoroimide and hydrogen fluoride (HF) as a by-product. This method is significantly disadvantageous since HF is a very hazardous by-product. In another method, R. E. Banks et al. disclose preparing perfluoro-[N-fluoro-N-(4-pyridyl)methanesulphonamide] (III) by fluorination of the sodio derivative of perfluoro-[N-(4-pyridyl)methanesulphonamide] in pure acetonitrile solvent. Banks et al. also note that theoretically $(CF_3SO_2)_2NH$ might be convertable to $(CF_3SO_2)_2NF$ via the sodium salt $(CF_3SO_2)_2NNa$.

In spite of the novel fluorinating compounds and the above methods of preparation, advancement is still sought in this field for improved synthesis steps which reduce processing and handling requirements, environmental hazards and costs associated with commercial processing methods. Such advancement is provided by the present invention.

SUMMARY OF INVENTION

The present invention has improved upon this technology by reacting a metal salt of the sulfonimide with fluorine in the presence of an effective solvent yielding the N-fluorosulfonimide and metal fluoride as depicted by the following equation.

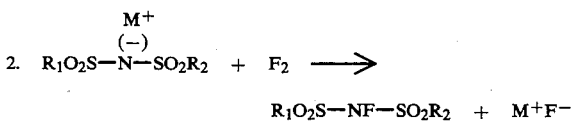

2. $R_1O_2S-\underset{\underset{(-)}{M^+}}{N}-SO_2R_2 + F_2 \longrightarrow$ $R_1O_2S-NF-SO_2R_2 + M^+F^-$ The fluorine reactant may be an isotope (e.g. radioactive fluorine: $^{18}F$) or isotopic mixture of fluorine. In equation 2, M is an alkali metal and preferably, is Li, K or Na, with the Na being the most preferred.

In equation 2 (and also in equation 1 supra), $R_1$ and $R_2$ independently can be phenyl or naphthyl, which is unsubstituted or substituted by $C_1$–$C_6$-alkyl, $C_1$–$C_6$-alkoxy, $C_1$–$C_6$alkylsulfonyl, $C_1$–$C_6$-perfluoroalkylsulfonyl, $C_1C_6$-mono to per-fluoroalkyl, cyano, fluoro, chloro, or bromo and is a metal selected from sodium, potassium or lithium.

The sulfonimide reactant used can also have the following formula:

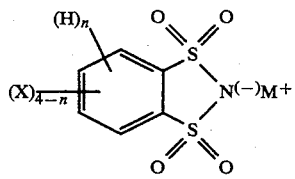

wherein X is selected from halogen, nitro, $C_1$–$C_6$ alkyl, $C_1$–$C_6$ alkoxy or halogenated $C_1$–$C_6$ alkyl and preferably, is selected from H, Cl, Br, F, $C_1$–$C_3$ alkyl, $C_1$–$C_3$ alkoxy or perfluoroalkyl($C_1$–$C_3$). More preferably, H, Cl, Br, F, $CH_3$, $CH_3O$, or $CF_3$. In the formula, n is an integer from 0 to 4 and preferably, n ranges from 1 to about 4. More preferably, n ranges from 2 to about 4, with n equal to 4 being the most preferred.

For preparation of compounds of the preceding formula, see Davis et al, *Tetrahedron Letters*, 32, No. 13, 1631–1634 (1991), which is incorporated herein.

As used herein an "effective" solvent is a water or water/organic solvent mixture wherein at least 10% (v/v) of the solvent mixture is water. The presence of the water significantly enhances the solubility of the sulfonimide reactant of equation 2. The process also has significant cost advantages since solvent costs are reduced by replacement of all or a portion of the organic solvent with water. This method is advantageous because the reaction avoids hazardous HF as a by-product. In addition, the method allows the fluoroimide to be prepared in greater yields and superior purity than methods of the prior art.

Organic solvents which can be used are those which are sufficient to solubilize the reactants under process conditions. A preferred organic solvent is acetonitrile. Other solvents in addition to water and acetonitrile include solvents such as propionitrile, acetic acid, methanol and mixtures thereof.

In preferred embodiments, at least about 25% of the solvent mixture is water, and more preferably, at least about 40% is water. In further preferred embodiments, the solvent mixture comprises at least about 50% water, and in particularly preferred embodiments, the solvent mixture comprises at least about 65%. In particularly preferred embodiments, the solvent mixture comprises at least about 75 to about 99% water with the solvent of choice being greater than 99% water or 100% water.

A preferred embodiment of the invention is when $R_1$ and $R_2$ in equation 2 are identical, preferably phenyl, unsubstituted or substituted. Substituents may be alkyl, alkoxy, alkylsulfonyl, perfluoroalkylsulfonyl, mono- to per-fluoroalkyl, containing 1–4 C-atoms in the alkyl groups. Examples of alkyl are methyl, ethyl, n-propyl and isopropyl; preferred examples are methyl and ethyl; examples of alkoxy are methoxy and ethoxy; examples of alkysulfonyl are methylsulfonyl and ethylsulfonyl; examples of perfluoroalkylsulfonyl are trifluoromethylsulfonyl and pentafluoroethylsulfonyl; examples of fluoroalkyl are fluoroethyl, 1,1-difluoroethyl, 1,2-difluoroethyl, 1,1,1-trifluoroethyl, 1,1,2,2-tetrafluoroethyl, perfluoroethyl and trifluoromethyl. $R_1$ and $R_2$ can have one or more substitutents, preferably one or two. A more preferred group of compounds of formula I is phenyl, unsubstituted or substituted with $C_1$–$C_6$-alkyl, perfluoroalkyl, cyano, F, Cl or Br. A preferred group of substitutents is $C_1$–$C_6$-alkyl, trifluoromethyl, cyano, F, Cl or Br; and M is sodium.

Examples of compounds of formula I and N-fluoro-p-methoxy-, N-fluoro-p-ethoxy-, N-fluoro-p-methyl, N-fluoro-p-trifluoromethyl-, N-fluoro-p-ethyl-, N-fluoro-p-methylsulfonyl-, N-fluoro-p-perfluoroethylsulfonyl-, N-fluoro-p-cyano, N-fluoro-p-chloro-, and N-fluoro-p-bromo-benzenesulfonimide, N-fluoro-p-fluorobenzene sulfonimide.

The most preferred embodiment is when $R_1$ and $R_2$ are both phenyl; equation I then represents N-fluorobenzenesulfonimide (NFSi).

In equation 1, the fluorination method of preparing N-fluorosulfonimides employs the direct fluorination of sulfonimides (See Differding et al., "N-Fluoro-Benzene Sulfonimide—A Practical Reagent for Electrophilic Fluorinations" *SYNLETT*, March 1991, 187–189). This method produces HF as a by-product. In order to counteract the acidity, sodium fluoride is added to the reaction prior to fluorination. Sodium fluoride absorbs HF forming a relatively harmless salt, sodium bifluoride ($NaHF_2$). This approach works well in solvents such as R-11, R-113 or other chlorofluorocarbons which are unreactive to fluorine gas at low temperature (—40° C.) because these solvents do not complex with HF.

Acetonitrile fluorinations with $F_2$ produce HF by two routes. The $CH_3CN$ itself, even in relatively small amounts, will react with $F_2$ and so will any organic compound with replaceable hydrogens (as is the case with N-fluorosulfonimides). The problem arises from the fact that acetonitrile complexes with HF. The complex formed is very stable and separating the acetonitrile/HF complex from the desired product by distillation is virtually impossible without having detrimental affects on the product. We have found that NaF is an ineffective scavenger for HF when working in acetonitrile (i.e. the HF/acetonitrile complex is stronger then the complex HF forms with NaF).

Our method avoids unnecessary purification steps, which can often reduce yields. For example, the fluorination reaction of equation 1 would likely require purification by an recrystallization step to obtain a substantially pure product. Typically, recrystallization reduces product yields by 10–15%.

Another disadvantage encountered when scaling up the direct fluorination/pure acetonitrile approach as described by Differding is that product yields decline (about 45–50% is typical in ca. 0.25 mole experiment). We attribute this problem to increased concentrations of HF in the reaction medium and for this reason it is doubtful that this approach could be used to make commercial quantities of the fluoroimide.

However, a novel approach to preparing these compounds which circumvents these problems has been demonstrated. By reacting fluorine with the sodium salt of sulfonimides (see equation 2), little or no HF is formed, and in fact sodium fluoride an HF scavenger is the by-product. This is also true for the other alkali metal salts of sulfonimides.

This results in several advantages which are:
1. N-Fluorosulfonimides can be prepared in organic/water mixtures and water without employing time consuming and difficult purification procedures to remove HF.
2. The product can be prepared faster and more economically since the reaction can be run in concentrated solutions (Note: we have prepared much larger batches of N-fluorobenzenesulfonimide in smaller reaction vessels than by the method of direct fluorination in pure acetonitrile).
3. Hydrogen fluoride (HF) containing waste products, which are hazardous and costly to dispose of, are avoided.
4. Yields (as high as 90%) of N-fluorobenzenesulfonimide have been obtained using this novel approach.
5. Additionally, N-fluorosulfonimides can be prepared in water, since the sodium salts of the imides are water soluble. Aryl sulfonimides tend to be water-insoluble and must be prepared in organic solvents which are costlier and in some cases toxic, and must be recovered by some process method (e.g. distillation).

The main advantage to preparing these compounds in water is that the isolation of the fluoroimide is greatly simplified. N-Fluorobenzenesulfonimide is insoluble in water; therefore, recovery may be accomplished by filtering, water washing and drying. Using this technique, yields of 90% have been achieved in the laboratory.

Also N-fluorosulfonimides, especially N-fluorobenzenesulfonimide can be prepared by our process in water at 0°–30° C., preferably at 15°–25° C. When the reaction media is mixed such as 10% $CH_3CN$/90% water, temperatures for preparing can be as low as −15° C. When 50/50 $CH_3CN/H_2O$ is used the preparation temperature can range from about −20° to about 30° C.

The sodium salts of the imides can be made by reacting one mole of sodium hydroxide with one mole of the sulfonamide,

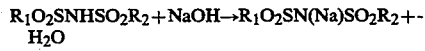

$R_1O_2SNHSO_2R_2 + NaOH \rightarrow R_1O_2SN(Na)SO_2R_2 + H_2O$ or by a known reaction between sodium benzenesulfonomide and benezenesulfonyl chloride. (N.N. Dyhanov Zhur. Obschei Khim. 29, 3602). Other metal salts of the imides can be formed by the above method, for example using potassium or lithium hydroxide. Other conventional methods of preparation for making the metal salts can also be employed.

EXAMPLE 1

This example demonstrates to the synthesis of N-fluorobenzenesulfonimide by using a sodium salt of the sulfonimide.

The sodium salt of benzenesulfonimide (16.0 g, 0.05 moles) was dissolved in 150 ml of 10% V/V water-/acetonitrile mixture. This was cooled to −10° C. and a gaseous mixture of 10% $F_2$ in nitrogen (V/V) was added at a rate of 100 cc/min. One equivalent of fluorine was added. The reaction was then evaporated to dryness, dissolved in methylene chloride, filtered to remove the insolubles (sodium fluoride) and then evaporated to dryness to get 13.5 g (85.7% yield) of N-fluorobenzenesulfonimide.

EXAMPLE 2 (COMPARATIVE)

This example demonstrates a preparation of N-fluorobenzenesulfonimide by the method disclosed by Differding in the prior art.

Benzenesulfonimide (5.95 g) was dissolved in 50 ml of acetonitrile and cooled to −23° C. Sodium fluoride (8.4 g) was added and a gaseous mixture of fluorine in nitrogen (10% V/V) was added at a rate of 100 co/min. for just over half an hour. The reaction liquor was evaporated to dryness and the resultant solid was washed 2×20 ml with diethyl ether. The product was dried to get 5.1 g (81% yield) of N-fluorobenzenesulfonimide; m.p. 113°–117° C.

EXAMPLE 3 (COMPARATIVE)

This example demonstrates the difficulty in the scale-up of the method of preparation used in Comparative Example 2.

Benzenesulfonimide (29.7 g, 0.1 mole) was dissolved in 200 ml of acetonitrile and cooled to −38° C. Sodium fluoride (21.0 g) was added and a mixture of fluorine in nitrogen (10% V/V) was added at a rate of 100 cc min. After two hours (1.07 equivalents $F_2$) fluorination was stopped and the reaction liquor was filtered and then evaporated to dryness. The resulting solid was washed twice with diethyl ether to remove impurities and then vacuum dried. A light yellow powder (13.6 g) was recovered for a 43.2% yield of N-fluorobenzenesulfonimide. The yield is lower than found in Comparative Example 2.

EXAMPLE 4

This example demonstrates the preparation of N-fluorobenzenesulfonimide using a 50/50 (V/V) water-/acetonitrile mixture.

Sodium benzenesulfonimide (16.0 g, 0.05 moles) was dissolved in 150 ml of 50/50 (V/V) water/acetonitrile mixture and cooled to −8° C. A gaseous mixture of fluorine in nitrogen (10% V/V) was added to the mixing suspension at the rate of 100 cc./min. After 1.65 equivalent of fluorine had been added the reaction was stopped, purged with nitrogen, and then filtered to get 12.6 g (79.8% yield) of N-fluorobenzenesulfonimide.

EXAMPLE 5

This example demonstrates a preparation of N-fluorobenzenesulfonimide using a 90/10 (V/V) water-/acetonitrile mixture.

Sodium benzenesulfonimide (16.0 g, 0.05 moles) were dissolved in 200 ml of water (90%) and acetonitrile (10%; V/V). After cooling to 5° C. a gaseous mixture of fluorine in nitrogen (10% V/V) was added at a rate of 200 cc/min. After 1.8 equivalents of $F_2$ had been added, the reaction was stopped, purged with nitrogen and filtered to get 5.1 g (94% yield) of N-fluorobenzenesulfonimide.

EXAMPLE 6

This example demonstrates the large scale preparation of N-fluorobenzenesulfonimide using a 100% water and no co-solvent.

Sodium benzenesulfonimide (63.8 g) was dissolved in 400 ml of water. A gaseous mixture of fluorine in nitrogen (10% V/V) was added at a rate of 300 cc/min. After 1.8 equivalent of $F_2$ had been added, the reaction was stopped, purged with nitrogen and filtered to get 56.0 g (88.9% yield) of N-fluorobenzenesulfonimide.

EXAMPLE 7

Preparation of N-fluoro-p-chlorobenzenesulfonimide.

The sodium salt of p-chlorobenzenesulfonimide (0.1 moles) was dissolved in 500 mL of a 60:40 mixture of water:acetonitrile. A gaseous mixture of fluorine in nitrogen (10% v/v) was added at a rate of 40 cc/min while maintaining the temperature between 0° C. and 5° C. After 1, hour, the reaction was purged with nitrogen, evaporated and titrated with acetonitrile to afford 23.5 g (61% yield) of N-fluoro-p-chlorobenzene-sulfonimide.

EXAMPLE 8

Preparation of N-fluoro-p-methylbenzenesulfonimide.

The sodium salt of p-methylbenzenesulfonimide (9 g; 0.03 mole) was dissolved in 150 mL of water and the pH adjusted to 9 with 5% aqu. NaOH. A gaseous mixture of fluorine in nitrogen (10% v/v) was added at a rate of 21 cc/min while maintaining the temperature between 25° C. and 30° C. After 30 min., the reaction was purged with nitrogen, and filtered to afford 5.7 g (70% yield) of N-fluoro-p-methylbenzenesulfonimide.

EXAMPLE 9

Preparation of N-fluorobenzenesulfonimide using a Lithium or Potassium Salt of Benzenesulfonimide.

The process described in Example 6 can be adapted to prepare N-fluorobenzenesulfonimide from either the lithium or potassium salt of benezenesulfonimide by using similar molar ratios and concentrations.

EXAMPLE 10

Preparation of $^{18}$F-N-fluorobenzium sulfonmide.

The substitution of $^{18}$F enriched fluorine gas for the $F_2$ used in Example 6 will afford $^{18}$F-N-fluorobenzenesulfonimide.

EXAMPLE 11

Preparation of N-Fluoro-o-benzenedisulfonimide.

N-Fluoro-o-benzenedisulfonimide can be prepared from either the sodium, lithium or potassium salt of o-benzenedisulfonimide by employing the procedure in Example 6 and using similar molar ratios and concentrations.

What is claimed is:

1. A process of preparing N-fluorosulfonimides comprising reacting an alkali metal salt of a sulfonimide with fluorine in the presence of water or an effective organic solvent/water mixture having at least 25% (V/V) of water in said mixture.

2. The process of claim 1 wherein alkali metal is selected from sodium, potassium or lithium.

3. The process of claim 1 wherein all or part of the fluorine reacted with the sulfonimide is radioactive fluorine ($^{18}$F).

4. The process of claim 1 wherein the alkali metal salt of the sulfonimide is a complex having one of the following formulas:

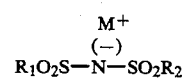

I wherein M represents sodium, potassium or lithium, and $R_1$ and $R_2$ independently are phenyl or naphthyl, which is unsubstituted or substituted by at least one substituent selected from the group consisting of alkyl groups having 1 to 6 carbon atoms, alkoxy groups having 1 to 6 carbon atoms, alkylsulfonyl groups having 1 to 6 carbon atoms, perfluoroalkylsulfonyl groups having 1 to 6 carbon atoms, mono- to per-fluoroalkyl groups having 1 to 6 carbon atoms, cyano, fluoro, chloro, and bromo; or

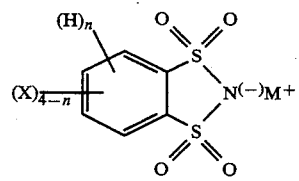

II wherein X is selected from halogen, nitro, $C_1$–$C_6$ alkyl, $C_1$–$C_6$ alkoxy or halogenated $C_1$–$C_6$ alkyl; and n is an integer from 0 to 4.

5. The process of claim 4 wherein $R_1$ and $R_2$ are the same.

6. The process of claim 5 wherein $R_1$ and $R_2$ are unsubstituted or substituted phenyl.

7. The process of claim 4 wherein $R_1$ and $R_2$ are phenyl or naphthyl which is unsubstituted or substituted by at least one substituent selected from the group consisting of alkyl groups having 1 to 6 carbon atoms, perfluoroalkyl groups having 1 to 6 carbon atoms, fluoro, cyano, chloro and bromo.

8. The process of claim 4 wherein $R_1$ and $R_2$ are phenyl which is unsubstituted or substituted by at least one substituent selected from the group consisting of alkyl groups having 1 to 6 carbon atoms, perfluoroalkyl groups having 1 to 6 carbon atoms, cyano, fluoro, chloro, and bromo.

9. The process of claim 1 wherein said reaction occurs in water or a mixture of water and at least one organic solvent selected from acetonitrile, propionitrile, acetic acid and methanol.

10. The process of claim 9 wherein the solvent mixture comprises at least about 25% (V/V) water.

11. The process of claim 9 wherein the solvent mixture comprises at least about 40% (V/V) water.

12. The process of claim 9 wherein the solvent mixture comprises at least about 50% (V/V) water.

13. The process of claim 9 wherein the solvent mixture comprises at least about 65% (V/V) water.

14. The process of claim 9 wherein the solvent mixture comprises at least about 75% to about 99% (V/V) water.

15. The process of claim 10 wherein the organic solvent is acetonitrile.

16. The process of claim 1 wherein the solvent is water.

17. The process of claim 1 wherein the N-fluorosulfonimide formed is a compound of the following formula:

$$R_1O_2S-NX-SO_2R_2$$

wherein X represents an isotope or natural isotopic mixture of fluorine, and $R_1$ and $R_2$ independently are phenyl or naphthyl, which is unsubstituted or substituted by at least one substituent selected from the group consisting of alkyl groups having 1 to 6 carbon atoms, alkoxy groups having 1 to 6 carbon atoms, alkylsulfonyl groups having 1 to 6 carbon atoms, perfluoroalkylsulfonyl groups having 1 to 6 carbon atoms, mono- to perfluoroalkyl groups having 1 to 6 carbon atoms, cyano, fluoro, chloro, and bromo.

18. The process of claim 17 wherein $R_1$ and $R_2$ are the same.

19. The process of claim 18 wherein $R_1$ and $R_2$ are unsubstituted or substituted phenyl.

20. The process of claim 17 wherein $R_1$ and $R_2$ are phenyl or naphthyl which is unsubstituted or substituted by at least one substituent selected from the group consisting of alkyl groups having 1 to 6 carbon atoms, perfluoroalkyl groups having 1 to 6 carbon atoms, fluoro, cyano, chloro and bromo.

21. The process of claim 17 wherein $R_1$ and $R_2$ are phenyl which is unsubstituted or substituted by at least one substituent selected from the group consisting of alkyl groups having 1 to 6 carbon atoms, perfluoroalkyl groups having 1 to 6 carbon atoms, cyano, fluoro, chloro and bromo.

22. The process of claim 17 wherein said compound is selected from the group consisting of N-fluoro-p-methoxy-benzenesulfonimide,
   N-fluoro-p-ethoxy-benzenesulfonimide,
   N-fluoro-p-methyl-benzenesulfonimide,
   N-fluoro-p-ethyl-benzenesulfonimide,
   N-fluoro-p-methylsulfonyl-benzenesulfonimide,
   N-fluoro-p-perfluoroethylsulfonyl-benzenesulfonimide,
   N-fluoro-p-cyano-benzenesulfonimide,
   N-fluoro-p-chloro-benzenesulfonimide, or
   N-fluoro-p-bromo-benzenesulfonimide,
   N-fluoro-p-fluoro-benzenesulfonimide.

23. The process of claim 17 wherein said compound is N-fluorobenzenesulfonimide.

* * * * *